Figure 1:
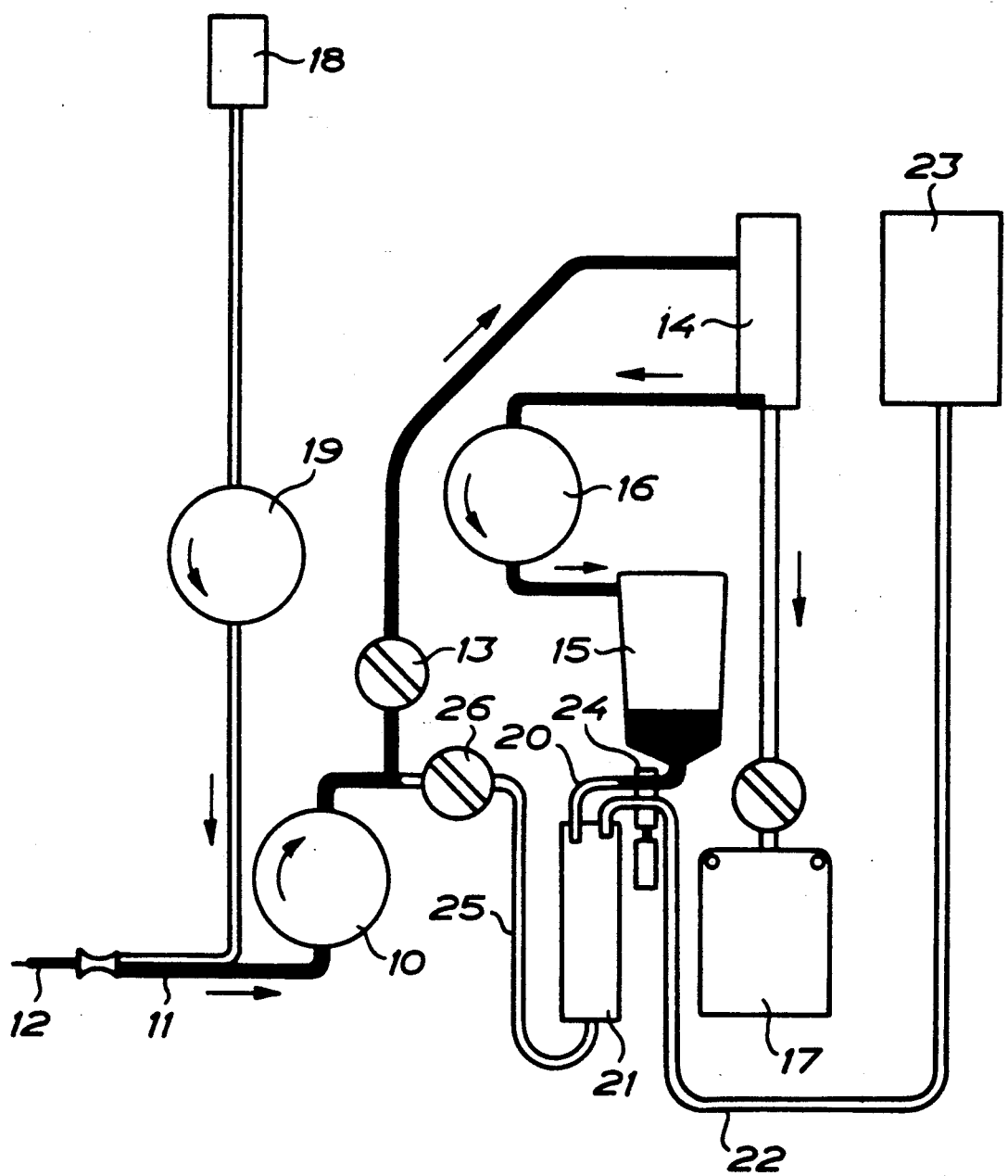

United States Patent [19]
Jonsson

[11] Patent Number: 5,098,372
[45] Date of Patent: Mar. 24, 1992

[54] METHODS AND MACHINE BASED ON BLOOD SEPARATION BY FILTRATION FOR PLASMA EXCHANGE TREATMENT, PLASMA DONATION AND CYTAPHERESIS SUCH AS PLATELET APHERESIS

[75] Inventor: Svante U. R. Jonsson, Glumslöv, Sweden

[73] Assignee: Stafilum AB, Uppsala, Sweden

[21] Appl. No.: 269,767

[22] PCT Filed: Apr. 24, 1987

[86] PCT No.: PCT/SE87/00218

§ 371 Date: Nov. 3, 1988

§ 102(e) Date: Nov. 3, 1988

[87] PCT Pub. No.: WO87/06471

PCT Pub. Date: Nov. 5, 1987

[30] Foreign Application Priority Data

Apr. 24, 1986 [SE] Sweden ................. 8601891

[51] Int. Cl.⁵ .............................. A61M 37/00
[52] U.S. Cl. .............................. 604/5; 604/4; 604/6
[58] Field of Search ................. 604/4, 5, 6; 128/DIG. 3

[56] References Cited

U.S. PATENT DOCUMENTS

| | | | |
|---|---|---|---|
| Re. 31,688 | 9/1984 | Popovich et al. | 604/6 |
| 3,482,575 | 12/1969 | Claff et al. | 604/4 |
| 4,086,924 | 5/1978 | Latham, Jr. | 604/6 |
| 4,185,629 | 1/1980 | Cullis et al. | 604/6 |
| 4,185,629 | 1/1980 | Cullis et al. | 604/6 |
| 4,648,866 | 3/1987 | Malbrancq et al. | 604/5 |
| 4,655,742 | 4/1987 | Vantard | 604/6 |
| 4,657,529 | 4/1987 | Prince et al. | 604/6 |

FOREIGN PATENT DOCUMENTS

| | | | |
|---|---|---|---|
| 0171749 | 2/1986 | European Pat. Off. | 604/6 |
| WO86/00231 | 1/1986 | PCT Int'l Appl. | |
| WO86/01426 | 3/1986 | PCT Int'l Appl. | |

OTHER PUBLICATIONS

FIG. 9G, Making Platelet Cut, p. 9.12 (Jan. 1977), Haemonetics Brochure, "Extended Storage Platelet ESP Pack".

Primary Examiner—Robert A. Hafer
Assistant Examiner—Kerry Owens
Attorney, Agent, or Firm—Merchant, Gould, Smith, Edell, Welter & Schmidt

[57] ABSTRACT

A machine for plasma exchange treatment, plasma donation, and cytapheresis such as platelet apheresis, having control means (24) for admixture of a liquid to flow of blood passing through a connection (25) between a pump (10) and a reservoir (15) for blood cells, associated with a separating means (14) for separation of blood by filtration into various components. The invention also relates to a method in operating such a machine, and a method for cytapheresis such as platlet apheresis, wherein said liquid is admixed to blood being drawn from a donor/patient and/or being returned from the separating process to the donor/patient.

3 Claims, 7 Drawing Sheets

METHODS AND MACHINE BASED ON BLOOD SEPARATION BY FILTRATION FOR PLASMA EXCHANGE TREATMENT, PLASMA DONATION AND CYTAPHERESIS SUCH AS PLATELET APHERESIS

The invention relates to a machine based on blood separation by filtration for plasma exchange treatment, plasma donation and cytapherasis such as platelet apheresis.

For plasma exchange treatment of a patient, whereby plasma is separated from the patient's blood (because the plasma may lack a certain substance or alternatively may contain substances(s) that cause(s) disease or may be generated by the disease and in turn give rise to significant troubles) and substitution fluid is added to the patient's blood, until now one has been forced to use machinery requiring two separate blood vessel connections through intravenous needles, catheters or the like, one connection for blood flow out from the patient and the other for the return flow back to the patient. This holds true irrespective of the principle applied for separation of blood, centrifugation or filtration. Dual connection has been the only feasible arrangement when running continuous blood separation processes by using equipment without reservoir functions. One special embodiment of plasma donation is so called plasma exchange donation wherein plasma is donated in exchange for the bulk of plasma collected from the donor at a preceding session, these plasma donors returning for donation once a month or much more often. Inbetween sessions the procured plasma is subjected to a sterile fractionation procedure such as taking out a so called cryoprecipitate, where concentrated coaguloation factor VIII may be found. Then the rest of the plasma may be returned without risk of any severe side effect to the donor. Therefore, thanks to the fully compatible exchange fluid being plasma, large volumes up to a few liters may be collected at advantage during each session.

An example of machinery that is capable of satisfactorily performing single-needle plasma donation using filtration as the principle for separating blood, is Autopheresis-C® made by Hemascience Inc., since 1986 Fenwal Automated Systems, Div. of Travenol Laboratories. It appears to represent the state of the art of blood filtration in applying modern computer control simultaneously of pump speeds, pressures, air in donor blood line etc and comprising a novel design of a filtration unit in which the membrane is rotating to minimize particle coating during filtration. Although the Autopheresis-C would fit the purpose of plasma exchange as far as drawing blood and filtration of blood for the collection of plasma for donation or as part of patient treatment, means and control means for infusing fluid in exchange for the relatively large volumes of plasma that may have to be taken out are lacking. Then, exchange fluid such as normal donor plasma might be given back through a separate needle or through a branch of the single blood line between the donor/patient and the machine, e.g. as a separate step manually controlled during or after return of concentrated blood. Aside from the manual control the drawbacks of designs like these are manifest by the return flow speed being limited, partly because the high viscoisity of (the first fraction of retransfused) packed red cells causes increased friction of flow and consequently increased internal pressure in the tubing and the receiving blood vessel, and partly because of the limited capacity of donors/patients to metabolize the calcium ion-binding citrate (admixed to blood during draw or generally to donated blood, inter alia as an inhibitor to coagulation), present in the plasma given (back) to the donor/patient (in exchange). A significant drawback of present single-needle techniques is the long time required for retransfusion.

During recent years a related medical procedure, viz. plasma donation as an alternative to whole blood donation, also has been automated with similar machines, which require but one syringe for vascular access, just as previously established as the routine for manual plasma donation. In such equipment, means for storing packed blood cells and means for periodically repeated retransfusion are mandatory, irrespective of the choice of principle for blood separation (centrifugation or filtration).

The primary purpose of the invention is to produce improved technical possibilities for rapid plasma exchange treatment, for some forms of plasma donation and for cytapheresis such as platelet donation and all as based on blood separation by filtration by utilizing but one blood vessel connection while eliminating or significantly reducing the drawbacks of presently existing equipment for these purposes.

For the attainment of this purpose the invention provides a machine for plasma exchange treatment, plasma donation and cytapheresis such as platelet apheresis, using filtration as the blood separation principle, comprising a donor tubing to be connected to a donor/patient for drawing blood therefrom and subsequently returning blood thereto, separating means for separating blood by filtration into various components of blood of which plasma is one, having a reservoir for blood cells, a pump capable of operating in two opposite directions, a first connection between said pump and said donor tubing, a second connection between said pump and said separating means, a third connection between said pump and said reservoir, a container for liquid, and a fourth connection from said container to said third connection, and control means for admixture of liquid from said container through said fourth connection to flow of blood passing through said connection. Beside the fact that such a machine may alternate between drawing blood from the patient/donor and retransfusing the concentrated blood less plasma and/or administer exchange fluid or plasma from that same individual or donor plasma back to him/her through one and the same tubing, according to the invention one may gain important advantages in addition to the treatment being simplified for the patient/donor and the personnel involved. When concentrated blood is given back to the patient/donor, in fact already by a small addition of saline solution (10-20 per cent) it may be diluted to the effect that the blood cells easier and quicker may pass into and through narrow tubing and blood vessels. Inversely, dilution of citrated plasma by simultaneous administration of packed blood cells makes the stress of a given amount of citrated plasma, which should be returned during each cycle, more tolerable, since that plasma volume is given back during a longer period of time without the treatment requiring longer overall time. Moreover, the increased retransfusion speed obtainable by mixing the two flows, according to our experience usually up to 130 ml per minute, causes the needle and/or catheter being part of the connection to the patient's blood vessel to be repeatedly flushed at high speed before each new draw phase. According to our experience, in this way one enjoys elimination or significant reduction of tendencies to obliteration of the patient connecting blood line, in particular of the needle, a problem often appearing during constant drawing of (not anticoagulated) blood from a patient/donor. Furthermore, if the needle/catheter is positioned in the blood vessel so that passage is narrow, it is usually much facilitated by dilution. Thus, increased counterpressure is avoided during retransfusion (particularly of the packed cells) through narrow passages and vessels as well as the related drawbacks.

The invention also provides a method in operating a machine for plasma exchange treatment, plasma donation and cytapheresis such as platelet apheresis, using filtration as the blood separation principle, comprising a donor tubing to be connected to a donor/patient for drawing blood therefrom and subsequently returning blood thereto, separating means for separating blood by filtration into various components of blood of which plasma is one, having a reservoir for blood cells, a pump capable of operating in two opposite directions, a first connection between said pump and said donor tubing, a second connection between said pump and said separating means, a third connection between said pump and said reservoir, a container for liquid, and a fourth connection from said container to said third connection, wherein liquid from said container is admixed through said fourth connection to flow of blood passing through said third connection.

Moreover the invention provides a method for plasma exchange treatment, plasma donation and cytapheresis such as platelet apheresis through a single needle connection with a donor/patient, comprising the steps of drawing blood from the donor/patient, separating by filtrating the blood into various components of which plasma is one, returning blood from the separation step to the donor/patient, and admixing a liquid to blood being returned to the donor/patient, as well as a method for cytapheresis such as platelet apheresis comprising the steps of drawing blood from a donor/patient, admixing plasma to said blood being drawn, separating by filtration the blood admixed with said plasma into various components of which plasma is one, said separated plasma being used also as the plasma admixed to the blood being drawn, and returning blood from the separation step to the donor/patient.

Figure 2:
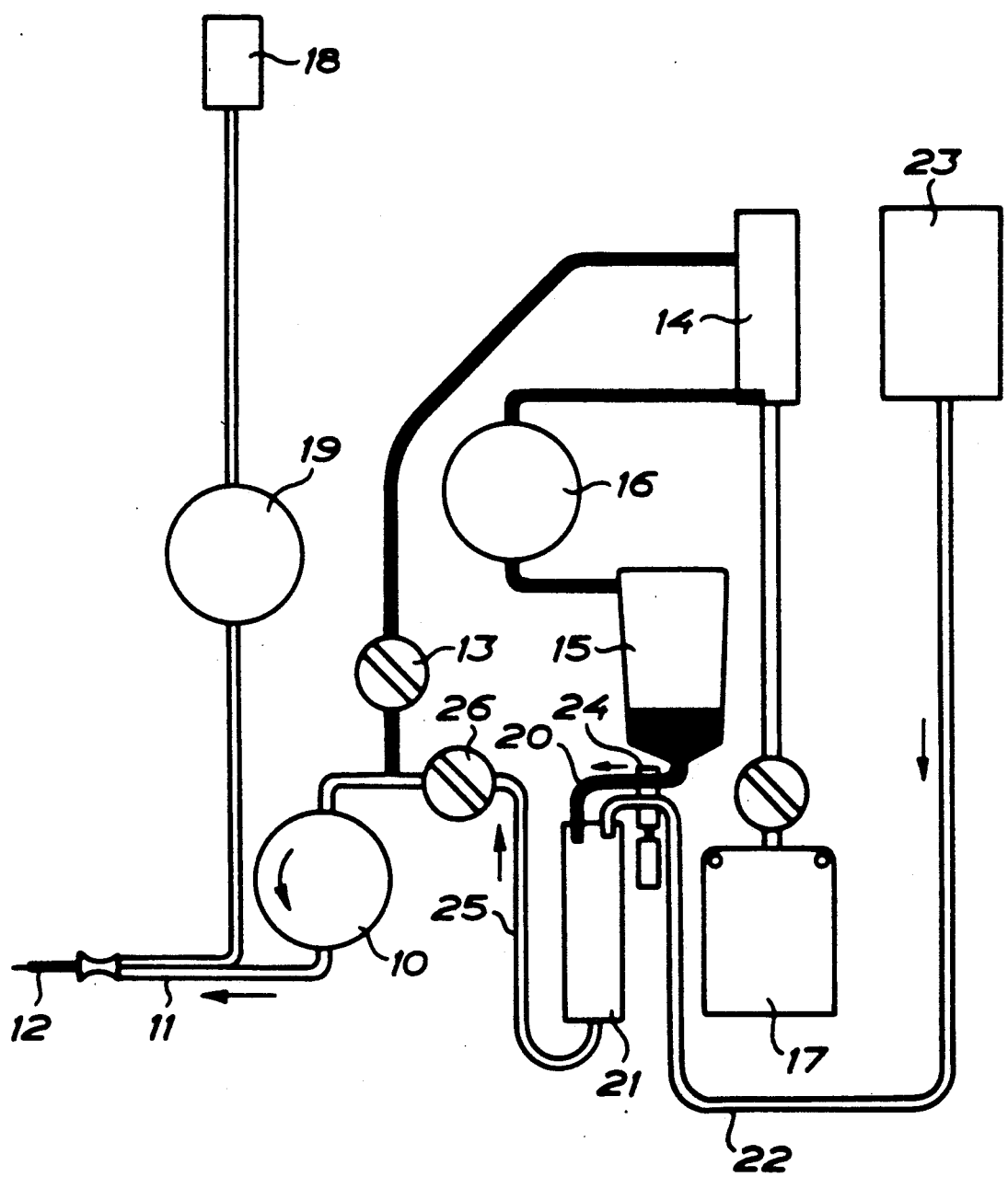
Figure 3:
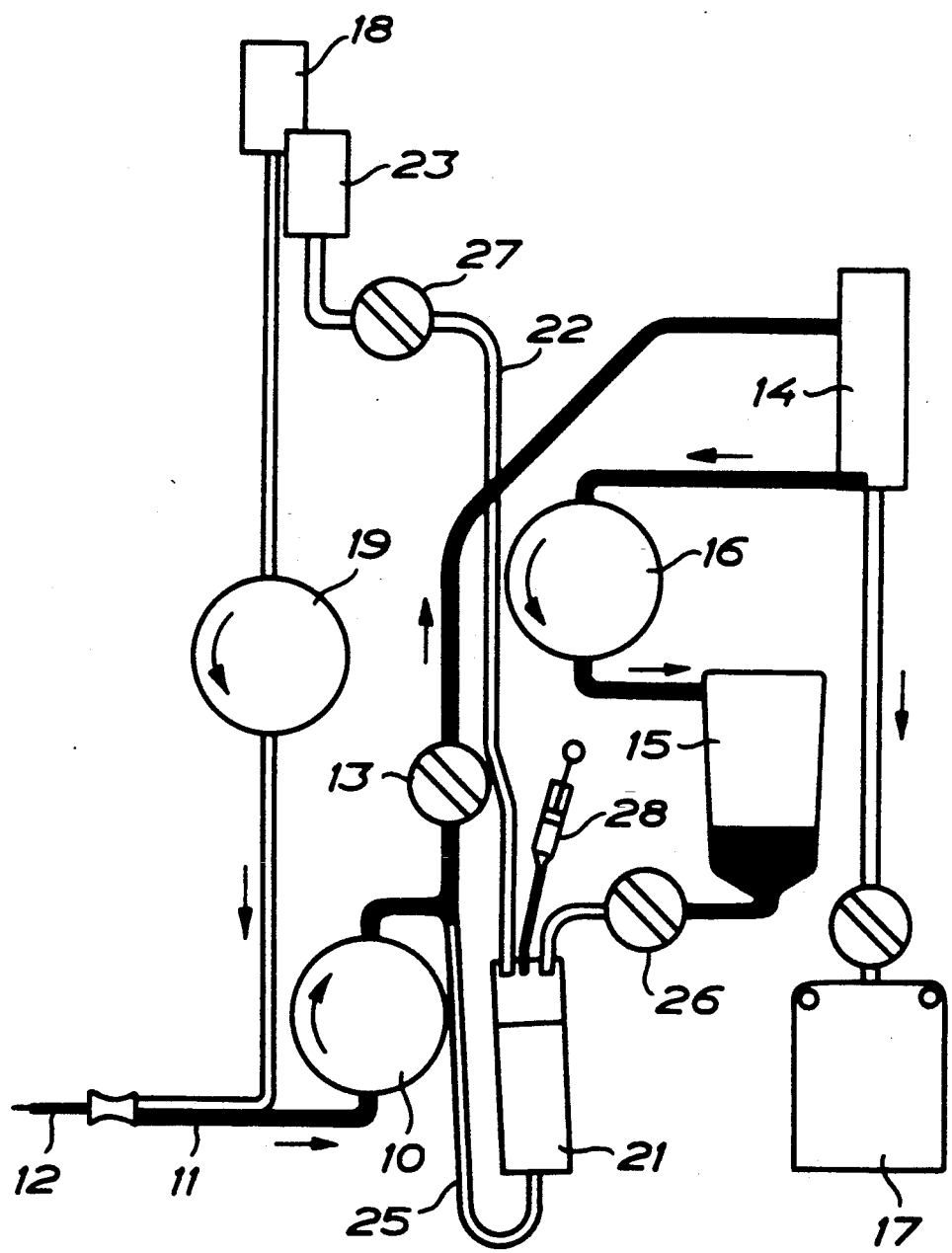
Figure 4:
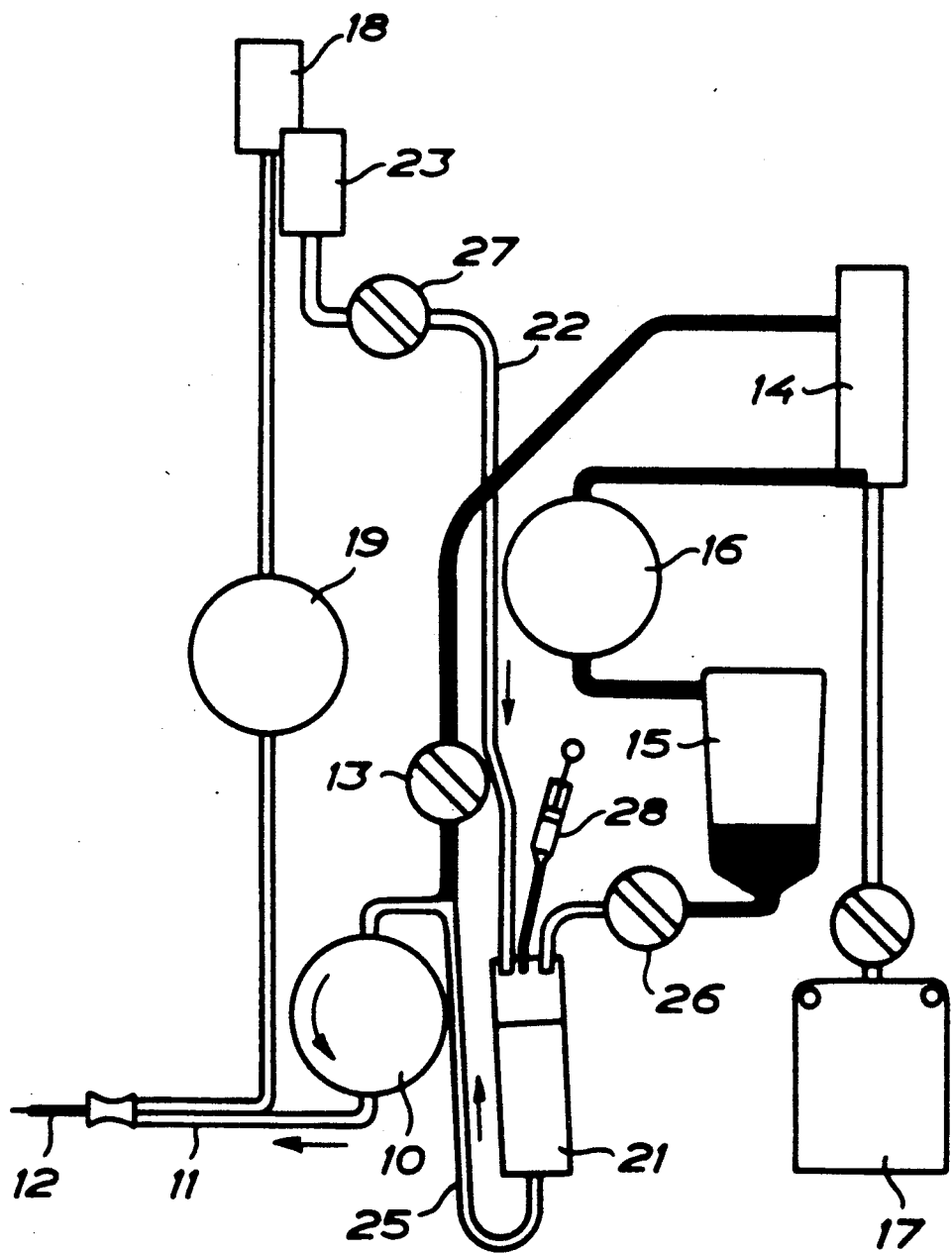
Figure 5:
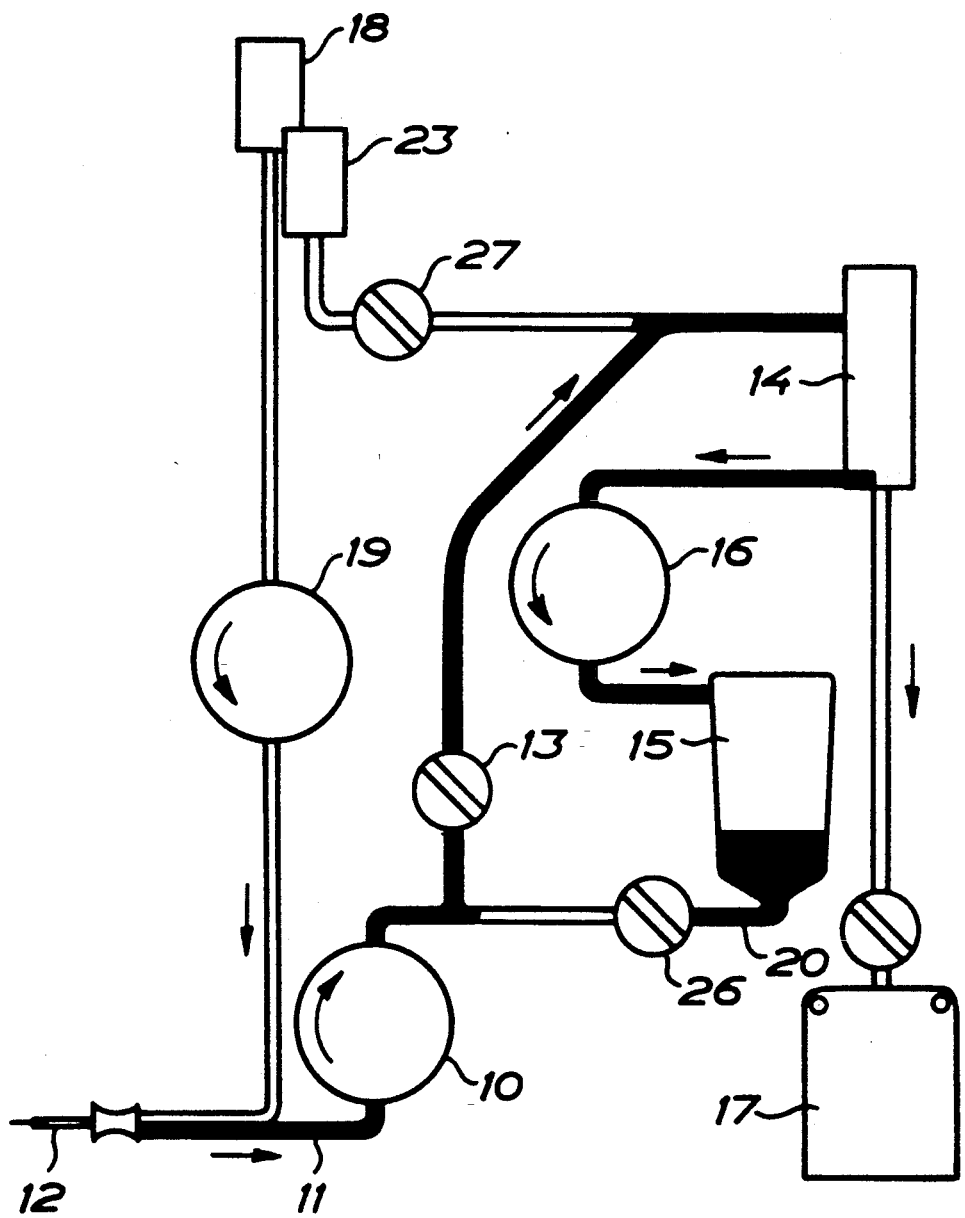
Figure 6:
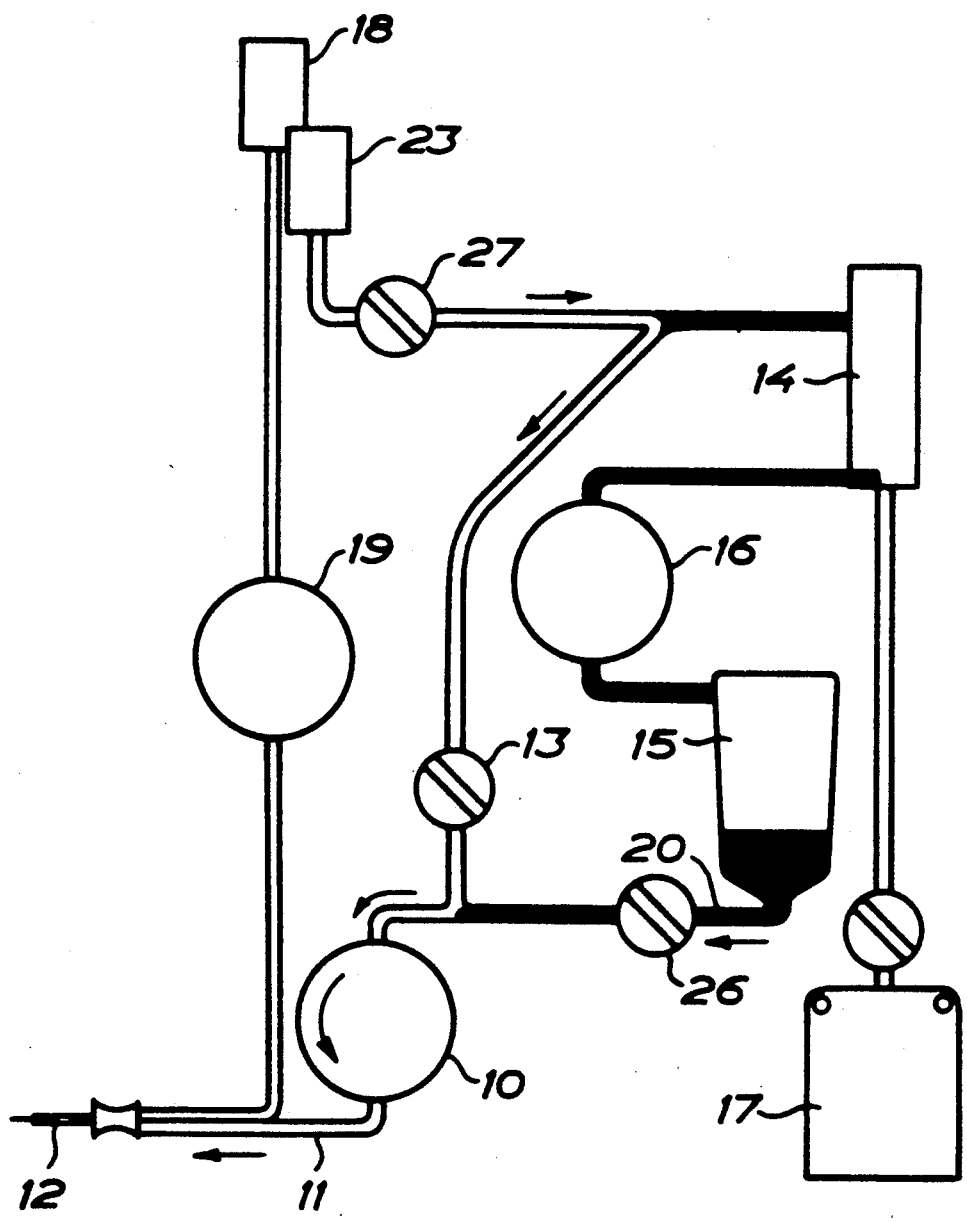
Figure 7:
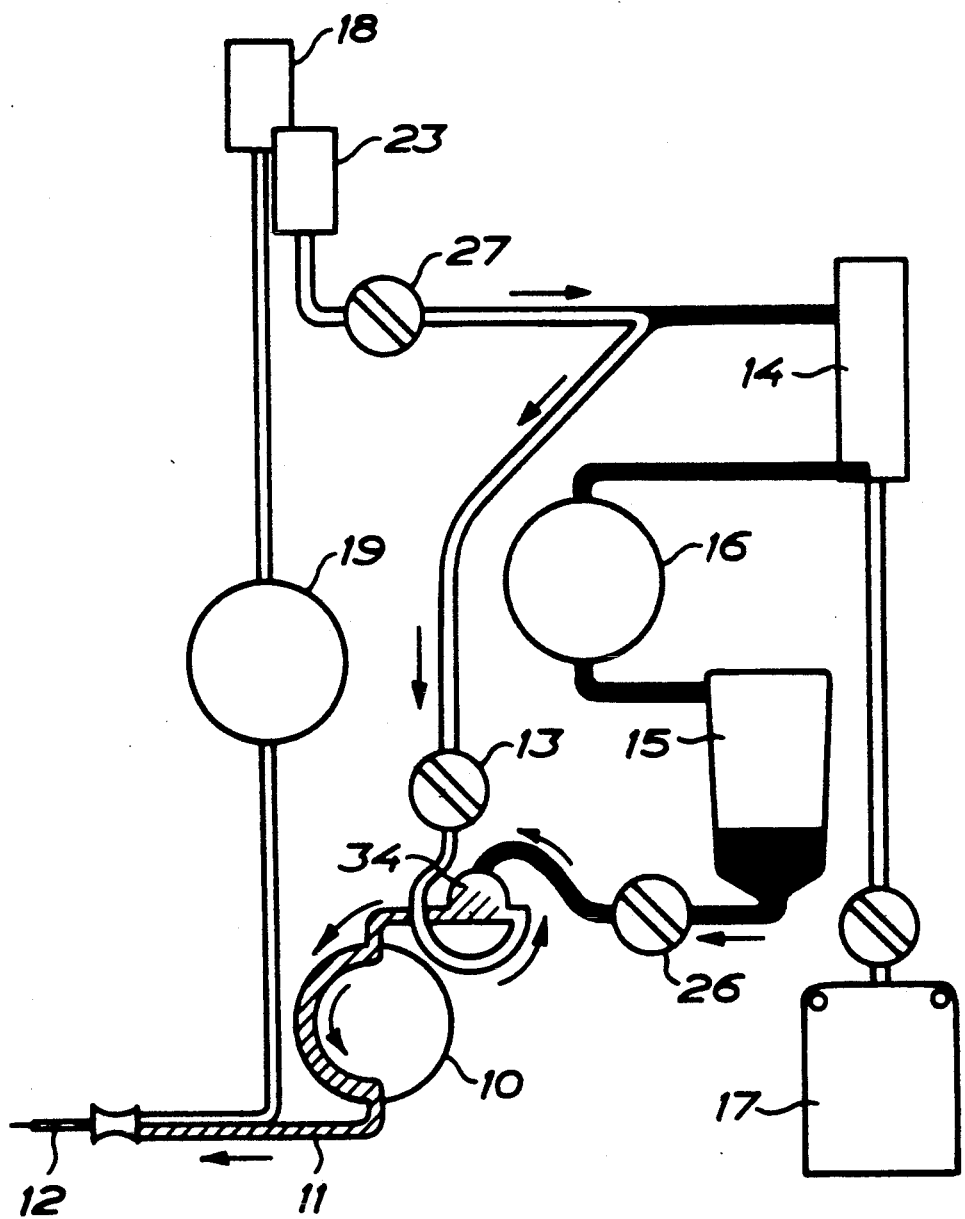

For a more detailed explanation of the invention reference is made to the accompanying diagrammatic drawings wherein FIGS. 1 and 2 disclose an embodiment of the machine according to the invention for plasma exchange treatment of patients in the functional position for drawing blood (FIG. 1) and in the functional position for administering blood and/or exchange fluid to the patient (FIG. 2);

FIGS. 3 and 4 disclose another embodiment of the machine in functional positions corresponding to FIG. 1 and FIG. 2, respectively;

FIGS. 5 and 6 disclose still another embodiment of the machine according to the invention in functional positions corresponding to FIG. 1 and FIG. 2, respectively; and FIG. 7 is a diagrammatic view similar to FIG. 6 disclosing a modification.

In the three embodiments disclosed in FIGS. 1-7 the machine is based on an existing machine for plasma donation, viz. AUTOPHESIS-C (TM) from HemaScience Laboratories Inc., Santa Ana, Calif. 92705, U.S.A., including a reversible peristaltic pump 10, one side of which is connected to a patient tubing 11 leading to/from the patient through a needle 12 for connection to a blood vessel of the patient/donor, while its other side via a pinch valve 13 is connected to means for separation by filtration of blood into different components. This means may be manufactured according to different established filtration principles, and in this case is shown as being of the type having a rotating filter 14 and, connected to the filter, a reservoir 15 for concentrated blood, a peristaltic pump 16 being arranged in the connection between the filter 14 and the reservoir 15. Furthermore, the filter is connected to a plasma recipient 17, usually constituted by a plastic blood bag, for the collection of plasma. To the needle 12 is also connected a container 18 for anticoagulant (usually a plastic bag containing sodium citrate solution) via a peristaltic pump 19.

The embodiment according to FIGS. 1 and 2 comprises a tubing 20 from a bottom outlet of the reservoir 15 leading to a mixing container 21 (drip chamber). To the latter there is also connected a tubing 22 from a container 23 (plastic bag) for substitution fluid (e.g. plasma or saline solution), the connection between the mixing container 21 on one hand and the reservoir 15 and the container 23, resp., on the other hand being controlled by means of a pinch valve 24, which shall keep the connecting tubing between the reservoir 15 and the mixing container 21 closed when the connection between container 23 and mixing container 21 is open, and vice versa. Advantageously, this valve is constructed according to Swedish patent 408 664. A tubing 25 extends from a bottom outlet of the mixing container 21, having a valve 26, and this tubing is connected to the tubing between the pump 10 and the valve 13. The embodiment as disclosed in FIGS. 1 and 2 is operated as follows. When drawing blood from the patient the pump 10 is operating in such a direction that it has its sucking side connected to the patient tubing 11 and its pressure side connected to the filter 14, the valve 13 being open and the valve 26 being closed. Blood is drawn from the patient/dorior and is supplied to the filter, anticoagulant solution being proportionally added to the blood from the reservoir 18 by way of the pump 19. The plasma separated from the blood in the filter 14 is collected in the plasma recipient 17 while the rest of the blood (concentrated blood) is supplied to the reservoir 15 by means of the pump 16, which is working with reduced speed as compared to the pump 10. In this working step of the procedure the position of the valve 24 is irrelevant since the valve 26 is closed.

After drawing blood has been continued during a suitable period of time, working step 2 of the procedure ensues according to FIG. 2. The pumps 16 and 19 are stopped, the valve 13 is closed and the valve 26 is opened, while the valve 24 is operated periodically, alternating between the position, in which the tubing connecting container 23 and mixing container 21 is kept open and the tubing connecting reservoir 15 and the mixing container 21 is kept closed, and the opposite position, in which the tubing connecting the reservoir 15 and the mixing container 21 is open but the tubing connecting the container 23 and the mixing container 21 is pinched closed. The operating direction of the pump 10 is reversed so that the mixing container 21 is connected to the sucking side of the pump, while the tubing leading from the machine to the patient is connected to the pressure side of the pump. As a consequence of the periodic change of positions of the valve 24 the mixing container 21 will receive alternately concentrated blood and substitution fluid for administration to the patient through the patient tubing 11 and needle 12 along with the blood, now thinner from dilution with substitution fluid. The periods of keeping the valve 24 in one and the other position, respectively, need not be the same, but it is possible by control of these periods to control the degree of dilution of blood according to intentions in the case of treatment.

For rapid infusion of fluid it is required that it is pre-warmed to between 30 and 37 centigrades. Thus, means for heating may be attached and integrated into the tubing 22. Since the container 23, as is usually the case, often is a plastic bag, air may have entered through the plastic film to be physically dissolved in the fluid during storage in that bag. Then, when the fluid is heated, such air will be liberated and form bubbles, which must be eliminated before administration of the fluid to the patient. This may be achieved by equipping the mixing container 21 (drip chamber) with means for deseration (28 of FIG. 3).

The embodiment of FIGS. 3 and 4 is largely identical to the embodiment of FIGS. 1 and 2, but the valve 24 is eliminated and instead the valves 26 and 27 are utilized, both part of the original machine for plasma donation, AUTOPHERESIS-C, on the basis of which the work leading to the present invention was started. In this embodiment valve 26 is positioned in the connection between the reservoir 15 and the mixing container 21.

When blood is drawn from the patient as shown in FIG. 3, the valve 13 is open, while the valves 26 and 27 are closed. Anticoagulant solution is proportionally administered by means of the the pump 19, and the pump 16 is operated as in the previous embodiment for supplying blood to the reservoir 15. Plasma is collected in the plasma recipient 17.

During retransfusion of blood and infusion of substitution fluid, FIG. 4, the pumps 16 and 19 are inoperative and the valve 13 is closed, while the valves 26 and 27 are controlled to be alternately open and closed to the effect that concentrated blood from the reservoir 15 during retransfusion is diluted with substitution fluid from the container 23, the two fluids being mixed in the mixing container 21 and the mixture being administered to the patient through the tubing 11 and the needle 12.

In this embodiment the mixing container 21 should be constructed as a fairly rigid drip chamber, to which a syringe 28 should be connected as a means for controlling the level of fluid in the container. This might be needed at irregular intervals, since the fluid arriving from the reservoir 23 liberates air from its bubbles as it drips down into the container 21. As the two valves 26 and 27 are opened and closed in alternating fashion, also in this embodiment the dilution of concentrated blood from the reservoir 15 with substitution fluid from the reservoir 23 is controlled by adjustment of the opening/closing intervals of these valves.

The embodiments as disclosed above according to the invention leads on to the extremely simple embodiment, which is disclosed in FIGS. 5 and 6. The existing machines that have been mentioned here and the modifications for the purposes of the invention according to FIGS. 1-4 have been produced in such manners that existing disposable sterile tubing sets made by Hema-Science Laboratories may be used. In the embodiments disclosed above some modification of the disposable set is required for the purposes of the invention, but for the embodiment according to FIGS. 5 and 6 such modification is not required.

In FIGS. 5 and 6 the machine is of type AUTOPHERESIS-C, and it is fitted in exactly the same way as when being used for plasma donation, but it is made to work in a modified manner. The machine is in principle the same as in FIGS. 1 and 2, but the mixing container 21 and the valve 24 are eliminated and the tubing 20 is connected directly to the valve 26. The container 23 is connected to the tubing between the valve 13 and the separation means 14. This is the way the machine is fitted when utilized for automated plasma donation. When drawing blood according to FIG. 5 the machine works in the same way as in FIG. 1 in that the valves 26 and 27 are closed. For the purpose of retransfusion according to FIG. 6 the pumps 16 and 19 stand still, and the direction of rotation of the pump 10 is reversed. The valve 27 is open, while the valves 13 and 26 are opened and closed alternately in relation to each other in the way disclosed above, suitably alternating approximately 10 times per minute or more. When the valve 26 is open and the valve 13 is closed, the pump 10 will draw concentrated blood from the reservoir 15, and when the valve 13 is open and the valve 26 is closed, the pump initially will draw the small amount of blood standing in the tubing between valve 13 and the filter 14 and thereafter substitution fluid from the reservoir 23. In order that the machine may work this way a modification of the control means of the machine (the software) is required. However, no mechanical modifications or additions and, in particular, no modification of the disposable tubing set will be necessary except at peripheral couplers for practical reasons such as sterility requirements.

One practical modification of the disposable tubing set proper, not only motivated for plasma exchange but also potentially advantageous in plasma donation, is a little bubble trap, which also may work as a small mixing chamber. It might simply be a modified tubing branch with an internal volume of a few ml and preferably made tapering towards the three branching ends or it may be shaped as a small dome as shown in FIG. 7 at 34. This modified branching device is then introduced at the connection point between the three tubing lines arriving from the pump 10, and the valves 13 and 26, resp. One of the ends of the tripartite branching chamber is directed upwards and is preferably connected to the blood reservoir or to the filtration unit so that air bubbles which may enter the chamber with the flow between the other two ends will be collected in this upper branch during retransfusion and so that these air bubbles in the beginning of each following draw phase be supplied to the reservoir 15 for concentrated blood, either directly via the valve 26 through the tubing 20 or via the valve 13 through the separation means 14 and from there via the pump 16 to the reservoir 15 for deseration via an air filter on top of this reservoir.

I claim:

1. Machine for plasma exchange treatment, plasma donation and cytapheresis, such as platelet apheresis, using filtration as the blood separation principle, comprising a donor tubing to be connected to a donor/patient for the drawing of blood therefrom and subsequent return of blood thereto; separating means for separation of blood by filtration into various components of which plasma is one, wherein said separating means has a reservoir for blood cells; a pump capable of operating in two opposite directions; a first connection between said pump and said donor tubing; a second connection between said pump and said separating means; a third connection between said pump and said reservoir; and a container for liquid; characterized by a fourth connection from said container to said third connection and a control means for admixture of liquid from said container through said fourth connection to flow of blood passing through said third connection.

2. Machine as in claim 1 wherein said control means comprises means for opening and closing alternately and repetitively said third connection and said fourth connection, respectively.

3. Machine as in claim 1, wherein said control means comprises a peristaltic pump for driving a flow of liquid through said fourth connection, and means controlling the operation of said pump.

* * * * *

UNITED STATES PATENT AND TRADEMARK OFFICE
CERTIFICATE OF CORRECTION

PATENT NO. : 5,098,372
DATED : March 24, 1992
INVENTOR(S) : Svante Jonsson

It is certified that error appears in the above-identified patent and that said Letters Patent is hereby corrected as shown below:

Title page, item: [30] Sweden "8601891" should read --8601891--8--.

Abstract, line 10 "platlet" should read --platelet--.

Column 1, line 10 "cytapherasis" should read --cytapheresis--.

Column 1, line 15 "substances(s)" should read --substance(s)--.

Signed and Sealed this

Seventh Day of September, 1993

Attest:

BRUCE LEHMAN

*Attesting Officer*      *Commissioner of Patents and Trademarks*